US00PP30901P2

(12) United States Plant Patent
Hanes

(10) Patent No.: US PP30,901 P2
(45) Date of Patent: Sep. 24, 2019

(54) ***PELARGONIUM* PLANT NAMED 'PEQZ0042'**

(50) Latin Name: *Pelargonium interspecific*
Varietal Denomination: PEQZ0042

(71) Applicant: SYNGENTA PARTICIPATIONS AG, Basel (CH)

(72) Inventor: Mitchell E. Hanes, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/998,038

(22) Filed: Jun. 15, 2018

(51) Int. Cl.
*A01H 5/02* (2018.01)
*A01H 6/42* (2018.01)

(52) U.S. Cl.
USPC ..... Plt./324

(58) Field of Classification Search
USPC ..... Plt./263.1, 324
See application file for complete search history.

*Primary Examiner* — Susan McCormick Ewoldt
*Assistant Examiner* — Karen M Redden
(74) *Attorney, Agent, or Firm* — Dale Skalla

(57) ABSTRACT

A new *Pelargonium* plant named 'PEQZ0042' particularly distinguished by the pink flowers with a splash pattern held above the medium-green foliage, very heat and drought tolerant with continuous color through the most extreme summer heat, and exceptional edema tolerance on a well-branched plant habit.

1 Drawing Sheet

Latin name of the genus and species of the plant claimed: *Pelargonium interspecific.*

Varietal denomination: 'PEQZ0042'.

BACKGROUND OF THE NEW PLANT

The present invention comprises a new *Pelargonium*, botanically known as *Pelargonium interspecific*, and hereinafter referred to by the variety name 'PEQZ0042'.

'PEQZ0042' is a product of a planned breeding program. The new cultivar 'PEQZ0042' has pink flowers with a splash pattern held above the medium-green foliage, very heat and drought tolerant with continuous color through the most extreme summer heat, and exceptional edema tolerance on a well-branched, compact, freely flowering plant.

'PEQZ0042' originates from a hybridization in a controlled breeding program made in April 2013 in a greenhouse in Guatemala. The female parent was an unpatented, proprietary plant of *P. interspecific* parentage, identified as '11337-4' with rose splash florets.

The male parent of 'PEQZ0042' was an unpatented, proprietary plant of *P. interspecific* parentage identified as '11333-6' with pink splash colored florets, on a small plant that was moderate flowering, and was not heat tolerant. The resultant seed was sown in September 2013 in a greenhouse in Gilroy, Calif.

'PEQZ0042' was selected as one flowering plant within the progeny of the stated cross in January 2014.

The first act of asexual reproduction of 'PEQZ0042' was accomplished when vegetative cuttings were propagated from the initial selection in the February 2014 in a greenhouse in Gilroy, Calif.

BRIEF SUMMARY OF INVENTION

Horticultural examination of plants grown from cuttings of the plant initiated in May 2014 in Gilroy, Calif., and continuing thereafter, has demonstrated that the combination of characteristics as herein disclosed for 'PEQZ0042' are firmly fixed and are retained through successive generations of asexual reproduction.

'PEQZ0042' has not been observed under all possible environmental conditions. The phenotype may vary significantly with variations in environment such as temperature, light intensity, and day length.

A Plant Breeder's Right for this cultivar has not yet been applied for. 'PEQZ0042' has not been made publicly available prior to the effective filing date of this application, notwithstanding any disclosure that may have been made less than one year prior to the effective filing date of this application by the inventor or another who obtained 'PEQZ0042' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

Figure 1:
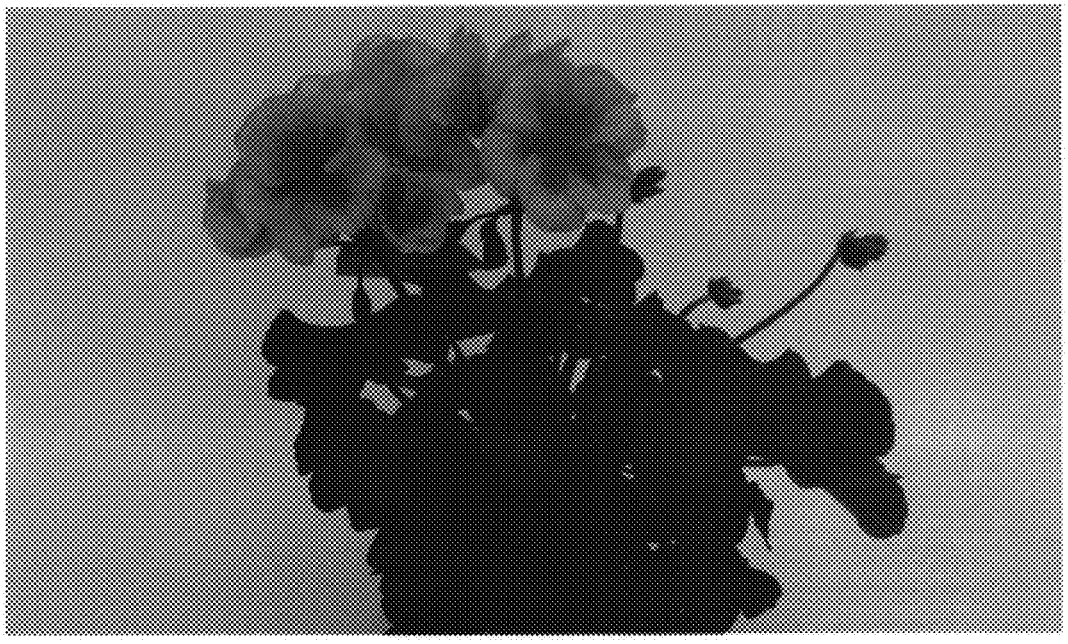
Figure 2:
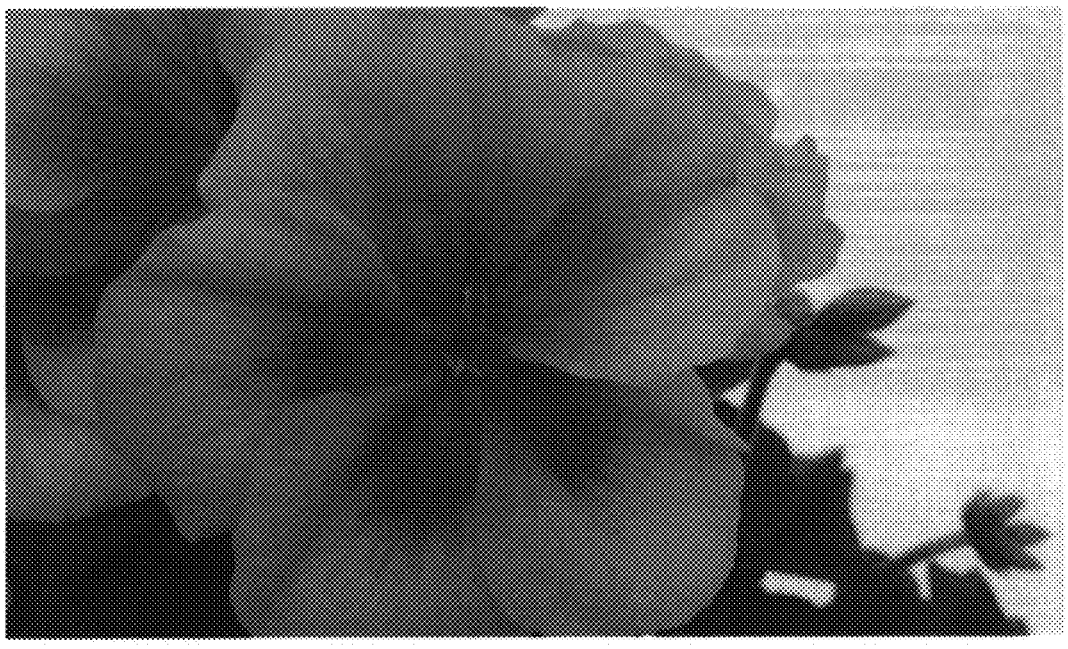

The accompanying photographic drawings show typical flower and foliage characteristics of 'PEQZ0042' with colors being as true as possible with an illustration of this type. The photographic drawings show in FIG. 1, a single plant with approximately 5 inflorescence stalks and in FIG. 2, a close-up of a single flower.

The plant descriptions, measurements, and photo were taken in Gilroy, Calif. in December 2017 under natural light. These plants were approximately 10 weeks old and were grown in a 4.5 inch pots, in a greenhouse trial.

Color references are made to The Royal Horticultural Society Colour Chart (R.H.S.) 2015.

DETAILED BOTANICAL DESCRIPTION

TABLE 1

DIFFERENCES BETWEEN THE NEW VARIETY 'PEQZ0042' AND A MOST SIMILAR VARIETY

| | 'PEQZ0042' | 'Calliope Medium Pink Flame', U.S. Pat. No. PP28,711, 'PEQZ0017' |
|---|---|---|
| Floret petal color: | Pink flowers with a splash pattern | Light pink flowers with a darker pink spot in the center of the petals |
| Plant height: | 14-16 cm | 22-28 cm |
| Plant width: | 29-37.0 cm | 55-60 cm |

Plant:

*Form, growth and habit.*—Compact plant with smaller flowers that is heat and drought tolerant with continuous color through the most extreme summer heat, edema tolerance, and freely flowering.

*Plant height.*—14-16.0 cm.

*Plant height (inflorescence included).*—23-25.0 cm.

*Plant width.*—29-37.0 cm.

Roots:

*Number of days to initiate roots.*—15-18 days at about 22 degrees C.

*Number of days to produce a rooted cutting.*—21-23 days at 22 degrees C.

*Type.*—Fine, fibrous, free branching.

*Color.*—RHS N155B but whiter.

Foliage:

*Immature leaf, color upper surface.*—RHS 143A.

*Immature leaf, lower surface.*—RHS 143D.

*Mature leaf, color upper surface.*—RHS 137C.

*Mature leaf, color lower surface.*—RHS 137D.

*Length.*—10-11.0 cm.

*Width.*—7.5-8.0 cm.

*Shape.*—Cordate to orbicular.

*Base shape.*—Cordate.

*Apex shape.*—Truncate to emarginate.

*Margin.*—Cilitate to dentate.

*Texture upper side.*—Hirsute.

*Texture lower side.*—Hirsute.

*Leaf zonation color.*—None.

*Color of veins, upper surface.*—RHS 137C.

*Color of veins, lower surface.*—RHS 137C.

*Pattern of veining.*—Palmate.

*Petiole color.*—RHS 137D.

*Petiole length.*—9.5-11.0 cm.

*Diameter of petiole.*—0.2-0.25 cm.

*Texture.*—Pilose, hirsute, glandular hairs.

Stem:

*Quantity of branches.*—4.

*Color of stem.*—Between RHS 144B.

*Length of stem.*—4-7.0 cm.

*Diameter.*—0.5-0.8 cm.

*Length of internodes.*—1-1.5 cm.

*Texture.*—Sparsely hirsute, pilose, glandular hairs.

Peduncle:

*Color of peduncle.*—RHS 137D.

*Length of peduncle.*—12-14.0 cm.

*Peduncle diameter.*—0.25-0.3 cm.

*Texture.*—Hirsute, glandular hairs.

Pedicel:

*Color of pedicel.*—RHS 137D turning to RHS 61A.

*Length of pedicel.*—2.5-4.0 cm.

*Diameter of pedicel.*—0.15-0.2 cm.

*Texture.*—Sparsely pilose, glandular hairs.

Bud (just before opening):

*Color.*—RHS N57C.

*Length.*—1.3-1.9 cm.

*Width.*—0.8-0.9 cm.

*Shape.*—Elliptical.

Inflorescence:

*Type.*—Umbel; semi-spherical or nearly semi-spherical.

*Lastingness of individual flowers.*—7-9 days at 18° C. temperature.

*Number of inflorescences per plant.*—6, with 4 immature umbels and 2 mature.

*Fragrance.*—None.

*Umbel diameter.*—9.0-11 cm.

*Umbel depth.*—6.5-7.5 cm.

Corolla:

*Form.*—Single to semi-double.

*Number of petals.*—5-7.

*Diameter of flower.*—5.5-6.0 cm.

*Depth of flower.*—1.5-2.0 cm.

*Color upper petals, upper surface.*—Closest to RHS 68B with RHS 45B spot.

*Color upper petals, lower surface.*—Closest to RHS 67C with RHS 45B spot.

*Length of upper petals.*—3.0 cm.

*Width of upper petals.*—2.5 cm.

*Color lower petals, upper surface.*—Closest to RHS 67C with RHS 45B spot.

*Color lower petals, lower surface.*—Closest to RHS 67C.

*Length of lower petals.*—2.5 cm.

*Width of lower petals.*—2.3 cm.

*Petal shape.*—Obovate to orbicular.

*Apex shape.*—Truncate.

*Margin.*—Entire.

*Base.*—Attenuate.

*Petal texture.*—Papillose on both surfaces.

Calyx:

*Number of sepals.*—5.

*Color of sepals.*—Between RHS 144A.

*Length of sepals.*—1.2-1.5 cm.

*Width of sepals.*—0.3-0.4 cm.

*Sepal shape.*—Lanceolate to linear.

*Apex shape.*—Apiculate.

*Margins.*—Mostly fused.

*Texture, upper surface.*—Glabrous.

*Lower surface.*—Glandular hairs, hirsute.

Reproductive organs:

Gynoecium:

*Pistil.*—1.

*Length.*—1.0 cm.

*Style color.*—Closest to RHS 53C.

*Style length.*—0.4 cm.

*Stigma color.*—Closest to RHS 53C.

*Ovary color.*—RHS 144A.

*Ovary length.*—0.4 cm.

*Ovary diameter.*—0.2 cm.

Androecium:

*Number of stamens.*—9.

*Color of filaments.*—RHS 67C with RHS 155C basally.

*Length filaments.*—0.8-1.0 cm.

*Anther color.*—RHS N30A.

*Length of anthers*.—0.2 cm.
*Color of pollen*.—RHS N30A.
*Pollen amount*.—Normal.
*Fertility/seed set*.—Has not been determined to date.
*Disease/pest resistance*.—Has not been determined to date.

What is claimed is:

1. A new and distinct variety of *Pelargonium* plant named 'PEQZ0042' substantially as illustrated and described herein.

* * * * *